(12) United States Patent
Vlutters et al.

(10) Patent No.: US 9,881,426 B2
(45) Date of Patent: Jan. 30, 2018

(54) 3D PATIENT INTERFACE DEVICE SELECTION SYSTEM AND METHOD

(71) Applicant: KONINKLIJKE PHILIPS N.V., Eindhoven (NL)

(72) Inventors: Ruud Vlutters, Eindhoven (NL); Karl Catharina Van Bree, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/890,044

(22) PCT Filed: Apr. 25, 2014

(86) PCT No.: PCT/EP2014/058412
§ 371 (c)(1),
(2) Date: Nov. 9, 2015

(87) PCT Pub. No.: WO2014/180671
PCT Pub. Date: Nov. 13, 2014

(65) Prior Publication Data
US 2016/0148437 A1    May 26, 2016

(30) Foreign Application Priority Data

May 10, 2013 (EP) ..................... 13167311
Jun. 7, 2013 (EP) ..................... 13170960

(51) Int. Cl.
G06K 9/00    (2006.01)
G06T 19/20    (2011.01)
(Continued)

(52) U.S. Cl.
CPC ............ *G06T 19/20* (2013.01); *A61B 5/1077* (2013.01); *A61M 16/06* (2013.01); *G06F 3/04815* (2013.01); *G06F 3/04842* (2013.01); *G06F 3/04847* (2013.01); *G06K 9/00281* (2013.01); *G06K 9/00288* (2013.01);
(Continued)

(58) Field of Classification Search
None
See application file for complete search history.

(56) References Cited

U.S. PATENT DOCUMENTS 7,827,038 B2    11/2010  Richard
8,634,900 B2 *   1/2014  Smith .................... A61B 5/015
                                                382/128

(Continued)

FOREIGN PATENT DOCUMENTS

EP       1116492 A2      7/2001
JP    2010131091 A      6/2010

*Primary Examiner* — Hadi Akhavannik
(74) *Attorney, Agent, or Firm* — Michael W. Haas

(57) ABSTRACT

An electronic apparatus for use in selecting a patient interface device and including a geometric fit score determining unit (42) configured to calculate a geometric fit score for each of one or more of patient interface devices, a patient criteria fit score determining unit (44) configured to calculate a patient criteria fit score for each of the one or more patient interface devices, and an overall fit score determining unit (46) configured to calculate an overall fit score for each of the one or more patient interface devices based on the calculated geometric fit score and the calculated patient criteria fit score for each of the one or more patient interface devices.

14 Claims, 11 Drawing Sheets

(51) Int. Cl.
  *G06T 19/00*     (2011.01)
  *A61M 16/06*     (2006.01)
  *A61B 5/107*     (2006.01)
  *G06F 3/0481*    (2013.01)
  *G06F 3/0484*    (2013.01)
  *G06T 7/33*      (2017.01)
  *A61B 5/00*      (2006.01)

(52) U.S. Cl.
  CPC .............. *G06T 7/344* (2017.01); *G06T 19/00* (2013.01); *A61B 5/0077* (2013.01); *A61M 2016/0661* (2013.01); *G06T 2200/24* (2013.01); *G06T 2207/10028* (2013.01); *G06T 2207/30201* (2013.01); *G06T 2210/41* (2013.01); *G06T 2219/2016* (2013.01)

(56)          References Cited

U.S. PATENT DOCUMENTS

| | | | |
|---|---|---|---|
| 9,582,706 B2 | 2/2017 | Van Bree | |
| 2004/0133604 A1 | 7/2004 | Lordo | |
| 2006/0023228 A1* | 2/2006 | Geng | A61B 5/411 356/601 |
| 2006/0235877 A1* | 10/2006 | Richard | A61M 16/06 |
| 2008/0060652 A1* | 3/2008 | Selvarajan | A61M 16/06 128/206.21 |
| 2009/0266362 A1* | 10/2009 | Mark | A61M 16/06 128/205.25 |
| 2015/0204663 A1 | 7/2015 | Znamenskiy | |

\* cited by examiner

3D PATIENT INTERFACE DEVICE SELECTION SYSTEM AND METHOD

CROSS-REFERENCE TO RELATED APPLICATIONS

This patent application claims the priority benefit under 35 U.S.C. §371 of international patent application no. PCT/EP2014/058412, filed Apr. 25, 2014, which claims the benefit of European Patent Application No. 13167311.3, filed on May 10, 2013 and European Patent Application No. 13170960.2, filed on Jun. 7, 2013. These applications are hereby incorporated by reference herein.

BACKGROUND OF THE INVENTION

1. Field of the Invention

The present invention pertains to a patient interface device selection system, and, in particular, to a patient interface device selection system that employs 3-D models.

2. Description of the Related Art

Obstructive sleep apnea (OSA) is a condition that affects millions of people from around the world. OSA is characterized by disturbances or cessation in breathing during sleep. OSA episodes result from partial or complete blockage of airflow during sleep that lasts at least 10 seconds and often as long as 1 to 2 minutes. In a given night, people with moderate to severe apnea may experience complete or partial breathing disruptions as high as 200-500 per night. Because their sleep is constantly disrupted, they are deprived of the restorative sleep necessary for efficient functioning of body and mind. This sleep disorder has also been linked with hypertension, depression, stroke, cardiac arrhythmias, myocardial infarction and other cardiovascular disorders. OSA also causes excessive tiredness.

Non-invasive ventilation and pressure support therapies involve the placement of a patient interface device, which is typically a nasal or nasal/oral mask, on the face of a patient to interface the ventilator or pressure support system with the airway of the patient so that a flow of breathing gas can be delivered from the pressure/flow generating device to the airway of the patient.

Typically, patient interface devices include a mask shell or frame having a cushion attached to the shell that contacts the surface of the patient. The mask shell and cushion are held in place by a headgear that wraps around the head of the patient. The mask and headgear form the patient interface assembly. A typical headgear includes flexible, adjustable straps that extend from the mask to attach the mask to the patient.

Because patient interface devices are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. Another concern is that an improperly fitted patient interface device can include gaps between the patient interface device and the patient that cause unwanted leakage. Thus, it is desirable to select a patient interface device that properly fits a patient.

A variety of different types or styles of patient interface devices are available. Additionally, a variety of different sizes of each type and style of patient interface device are available. Thus, the total number of distinct patient interface devices available to a patient can become quite large.

Caregiver's have generally assisted patients with the selection of a suitable patient interface device. The caregiver can take into account the patient's condition and preferences to narrow down the list of potential patient interface devices. The caregiver can also estimate the proper size of the patient interface device or have the patient try on several patient interface devices to determine the correct size. However, these methods can be time consuming and inaccurate.

US 2008/0060652 A1 discloses a system and method for selecting a mask system for a patient. This includes generating 3D contours of patients and selecting mask systems based at least on these contours. These contours may be generated by using, for example, a cushion of translatable pins, a nasal cannular scanning device, and/or a shadow stereopsis sensor. Certain other exemplary embodiments allow images and/or videos to be captured and optionally synchronized. Then, images of various mask systems may be overlaid to determine how well a mask system fits. In still other embodiments, a user can hold a transparency corresponding to a mask design in front of the patient's face to determine how well a mask system fits.

EP 1 116 492 A2 a method in which a spatial record of the area of a user's face around mouth and nose is recorded. Based on the spatial record, a sealing lip section of a breathing mask is formed so that it is matched to an individual's record.

US 2004/133604 A discloses a patient interface device selection system that includes a database storing a plurality of sets of data. Each set of data in the plurality of sets of data is associated with a unique patient interface device or a component thereof. A patient data collection system, such as a measuring device, acquires a set of patient data that correspond to at least one characteristic of a patient. A processing system compares the acquired patient data with the plurality of sets of data, and determines the patient interface device or the component thereof that is suitable for use by such a patient based on a result of the comparison.

Accordingly, a need exists for improvement in ways to select a suitable patient interface device for a patient.

SUMMARY OF THE INVENTION

In accordance with aspects of the disclosed concept, an electronic apparatus comprises a geometric fit score determining unit that is configured to receive a 3-D model of a patient's face and a plurality of 3-D models of patient interface devices, to determine one or more landmarks on the 3-D model of the patient's face, and to calculate a geometric fit score for each of one or more of the patient interface devices by using the 3-D model of the patient's face and the 3-D models of the one or more patient interface devices. The geometric fit score determining unit is further configured to fit a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device. The electronic apparatus further comprises a user interface generator configured to generate a user interface including a display area configured to display the 3-D model of the patient's face and a 3-D model of a patient interface device selected from the plurality of 3-D models of patient interface devices, and a patient interface device selection area configured to display patient interface device identification information and an overall fit score which is calculated for each of one or more patient interface devices based on the geometric fit score for each of the one or more patient interface devices and to allow a user to select the patient interface device to be displayed in the display area.

According to an embodiment, the electronic apparatus may further comprise a patient criteria fit score determining unit configured to receive patient information and/or additional information associated with the one or more patient interface devices, and to calculate a patient criteria fit score for each of the one or more patient interface devices based on the patient information and/or the additional information associated with the one or more patient interface devices, and an overall fit score determining unit configured to calculate an overall fit score for each of the one or more patient interface devices based on the calculated geometric fit score and the calculated patient criteria fit score for each of the one or more patient interface devices.

It should be clear that at least the overall fit score as displayed in the patient interface device selection area need not be a numerical value. Instead, it should be regarded as an indicator of a numerical fit score. Although the overall fit score might be represented as a numerical value, it might alternatively or additionally be displayed using, for instance, color coding, pictograms, etc. It might also be displayed as the length of a bar. The above also holds for the geometric fit score and the patient criteria fit score.

According to other aspects of the disclosed concept, a method of selecting a patient interface device comprises receiving a 3-D model of a patient's face; receiving a plurality of 3-D models of patient interface devices; determining one or more landmarks on the 3-D model of the patient's face; calculating a geometric fit score for each of one or more of the patient interface devices by using the 3-D model of the patient's face and the 3-D models of the one or more patient interface devices, wherein calculating the geometric fit score includes fitting a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device; calculating an overall fit score for each of the one or more patient interface devices based on the calculated geometric fit score for each of the one or more patient interface devices; generating a user interface, wherein generating the user interface comprises: generating a display area configured to display the 3-D model of the patient's face and a selected 3-D model of one of the patient interface devices; and generating a patient interface device selection area configured to display patient interface device identification information and the calculated overall fit score for each of the one or more patient interface devices and to allow a user to select the patient interface device to be displayed in the display area.

According to other aspects of the disclosed concept, a non-transitory computer readable medium stores one or more programs, including instructions, which when executed by a computer, causes the computer to perform the above-mentioned method.

According to other aspects of the disclosed concept, a method for selecting a patient interface device of a plurality of patient interface devices comprises creating a 3-D model of a patient's face; creating 3-D models of each of the plurality of patient interface devices; providing the 3-D model of the patient's face to a patient interface device selection system; providing one or more of the 3-D models of the patient interface devices to the patient interface device selection system; employing the patient interface device selection system to obtain an overall fit score for each of the one or more patient interface devices and to display the 3-D model of the patient's face with one or more of the 3-D models of the patient interface devices fitted thereon; and selecting one of the patient interface devices, wherein the patient interface device selection system comprises: a geometric fit score determining unit configured to receive the 3-D model of a patient's face and the one or more 3-D models of patient interface devices, to determine one or more landmarks on the 3-D model of the patient's face, and to calculate a geometric fit score for each of one or more of the patient interface devices by using the 3-D model of the patient's face and the one or more 3-D models of the patient interface devices, wherein the geometric fit score determining unit is configured to fit a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device; and a user interface generator configured to generate a user interface including a display area configured to display the 3-D model of the patient's face and a selected 3-D model of one of the patient interface devices, and a patient interface device selection area configured to display patient interface device identification information and the overall fit score which is calculated for each of the one or more patient interface devices based on the geometric fit score for each of the one or more patient interface devices and to allow a user to select the patient interface device to be displayed in the display area.

DETAILED DESCRIPTION OF EXEMPLARY EMBODIMENTS

Figure 1:
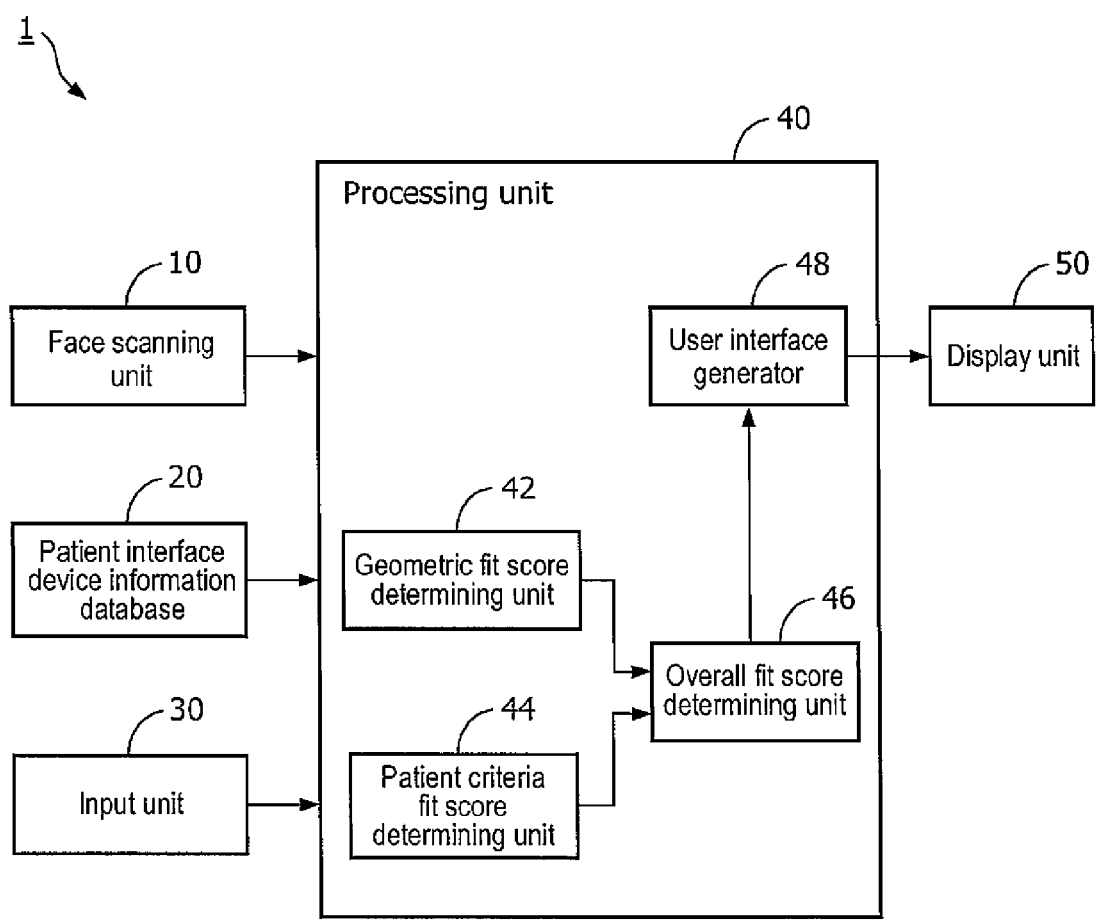
FIG. 1 is a diagram of a system for selecting a patient interface device according to one exemplary embodiment of the disclosed concept.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As employed herein, the terms "processor", "processing unit", and similar terms shall mean a programmable analog and/or digital device that can store, retrieve and process data; a controller; a control circuit; a computer; a workstation; a personal computer; a microprocessor; a microcontroller; a microcomputer; a central processing unit; a mainframe computer; a mini-computer; a server; a networked processor; or any suitable processing device or apparatus.

FIG. 1 is a block diagram of a patient interface device selection system 1 according to one exemplary embodiment of the disclosed concept. Patient interface device selection system 1 includes a face scanning unit 10, a patient interface device information database 20, an input unit 30, a processing unit 40, and a display unit 50.

Face scanning unit 10 is configured create and output a 3-D model of a patient's face. Devices are known that are capable of creating and outputting a 3-D model of a patient's face. Examples of such devices include, without limitation, optical scanners, cameras, and push-pin arrays. Face scanning unit 10 is communicatively coupled to processing unit 40 and is configured to output the 3-D model of the patient's face to the processing unit 40. It is contemplated that face scanning unit 10 and processing unit 40 can be at the same location or at different locations without departing from the scope of the disclosed concept. It is also contemplated that the face scanning unit 10 and processing unit 40 are communicatively coupled by any suitable means (e.g., without limitation, network, internet, USB, etc.). It is also contemplated that face scanning unit 10 can save the 3-D model of the patient's face to a removable memory device (e.g., without limitation, a USB drive) which can then be read by processing unit 40.

Patient interface device information database 20 is configured to store 3-D models of a number of patient interface devices and additional information associated with the patient interface devices. The 3-D models of the patient interface devices can be acquired by any suitable means. For example and without limitation, the 3-D models of the patient interface devices can be created using devices such as, without limitation, optical scanners, cameras, or push-pin arrays. It is also contemplated that the 3-D models of the patient interface devices can be computer generated (e.g., without limitation, created with 3-D modeling software).

In some exemplary embodiments of the disclosed concept, the 3-D models of the patient interface devices are configured such that individual components or groups of components of the 3-D models can be individually manipulated. For example, one exemplary 3-D model of a patient interface device includes a mask including a cushion, a support structure, a moveable forehead support including a forehead cushion, and an elbow conduit. The 3-D model of this patient interface can be configured such that, for example, the moveable forehead support can be individually moved with respect to other components.

In some exemplary embodiments of the disclosed concept, the 3-D models of the patient interface devices also include information about properties of the components of the patient interface devices. For example, the 3-D models of the patient interface devices can include information on properties such as, without limitation, elasticity of the cushion of the patient interface device.

The additional information associated with the patient interface devices includes information which rates the suitability of each patient interface device based on patient factors (e.g., without limitation, what type of condition the patient suffers from). The additional information associated with the patient interface devices also includes the patient interface device identification information (e.g., without limitation, the manufacturer name, product name, and size).

Patient interface device information database 20 is communicatively coupled to processing unit 40 and is configured to output the 3-D models and additional information to the processing unit 40. It is contemplated that patient interface device information database 20 and processing unit 40 can be at the same location or at different locations without departing from the scope of the disclosed concept. It is also contemplated that the patient interface device information database 20 and processing unit 40 are communicatively coupled by any suitable means (e.g., without limitation, network, internet, USB, etc.). In some other exemplary embodiments, patient interface device information database 20 is included in processing unit 40. It is also contemplated that patient interface device information database 20 can save the 3-D models of the patient interface devices to a removable memory device (e.g., without limitation, a USB drive) which can then be read by processing unit 40.

Input unit 30 is configured to receive input of a user of patient interface device selection system 1. Input unit 30 can be any conventional device capable of performing this function, such as, without limitation, a keyboard, keypad, mouse, or touch screen. Input unit 30 is communicatively coupled with processing unit 40 by any suitable means (e.g., without limitation, network, internet, USB, etc.).

Processing unit 40 is configured to receive outputs from face scanning unit 10, patient interface device information database 20, and input unit 30. Processing unit 40 includes a geometric fit score determining unit 42, a patient criteria fit score determining unit 44, an overall fit score determining unit 46, and a user interface generator 48, each of which will be described in more detail hereinafter.

Processing unit 40 can be, for example, any type of processing apparatus such as a microprocessor and a memory unit suitable to store and execute software modules. Geometric fit score determining unit 42, patient criteria fit score determining unit 44, overall fit score determining unit 46, and user interface generator 48 can each be embodied as software modules which are executable by the processing unit 40.

Geometric fit score determining unit 42 is configured to determine a geometric fit score for one or more of the patient interface devices. The geometric fit score for a respective patient interface device is a rating of how well the geometry of the patient's face and the geometry of the respective patient interface device fit together. Points of high contact pressure or gaps between the patient's face and the respective patient interface device would have a negative effect on the geometric fit score.

Figure 2:
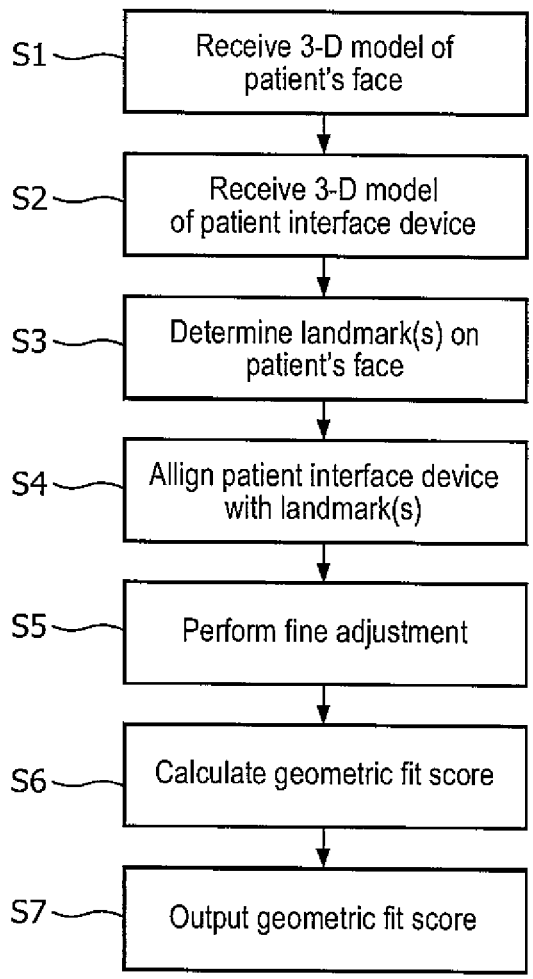
FIG. 2 is a flowchart of a method of determining a geometric fit score according to an exemplary embodiment of the disclosed concept.

FIG. 2 illustrates a flowchart of one exemplary process for determining a geometric fit score for a respective patient interface device. The process illustrated in FIG. 2 may be implemented by the geometric fit score determining unit 42. Referring to FIG. 2, the geometric fit score determining unit 42 receives the 3-D model of the patient's face in operation S1. In operation S2, the geometric fit score determining unit 42 receives a 3-D model of the respective patient interface device.

In operation S3, the geometric fit score determining unit 42 determines one or more landmarks on the 3-D model of the patient's face. Landmarks can be any distinctive feature on the patient's face (e.g., without limitation, bridge of the nose, tip of the nose, chin, etc.). In operation S4, selected points on the 3-D model of the respective patient interface device are aligned with the determined landmarks on the 3-D model of the patient's face. For example, an upper part of a cushion in the 3-D model of the respective patient interface device can be aligned with the bridge of the nose in the 3-D model of the patient's face. In operation S5, fine adjustment is performed on the 3-D model of the respective patient interface device. The 3-D model of the respective patient interface device is translated and rotationally adjusted to fit it to the 3-D model of the patient's face. For example and without limitation, the 3-D model of the respective patient interface device is rotated and translated to match the contour of the cushion with the contour of the 3-D model of the patient's face as best as possible. However, it is contemplated that any suitable method of finely adjusting the 3-D model of the respective patient interface device can be employed without departing from the scope of the disclosed concept.

Operations S3-S5 represent an exemplary process of fitting the 3-D model of the respective patient interface device to the 3-D model of the patient's face. However, it is contemplated that any suitable process of fitting the 3-D model of the respective patient interface device to the 3-D model of the patient's face may be employed without departing from the scope of the disclosed concept.

When the 3-D model of the respective patient interface device is fitted to the patient's face, the geometric fit score determining unit 42 calculates the geometric fit score for the respective patient interface device for the patient's face in operation S6. The geometric fit score is calculated based on the interaction between the 3-D model of the respective patient interface device and the 3-D model of the patient's face. In an exemplary embodiment, the geometric fit score is calculated based on differences between the contour of the cushion of the 3-D model of the respective patient interface device and the contour of the 3-D model of the patient's face. For example, when the 3-D model of the respective patient interface device is fitted to the 3-D model of the patient's face, any points where the contour of the cushion of the 3-D model of the respective patient interface device is above or below corresponding points on the contour of the 3-D model of the patient's face will adversely affect the geometric fit score for the respective patient interface device. It is also contemplated that calculation of the geometric fit score can take into account deformation of the respective patient interface device and the patient's face. For example, finite element methods can be employed to determine deformations in the patient interface device and patient's face when the 3-D model of the patient interface device is fitted on the patient's face.

In operation S7, the geometric fit score determining unit 42 outputs the calculated fit score to the overall fit score determining unit 46. It is also contemplated that the geometric fit score determining unit 42 can output additional information such as information on the placement of the 3-D model of the respective patient interface device when it is fitted on the 3-D model of the patient's face. This information can be used, for example, by the user interface generator 48 to create a 3-D display of the 3-D model of the respective patient interface device fitted on the 3-D model of the patient's face. It is also contemplated that the geometric fit score determining unit 42 can output information regarding levels of interaction between the 3-D model of the respective patient interface device and the 3-D model of the patient's face. This information can be employed, for example, to generate an interaction map between the respective patient interface device and the patient's face. Generation and display of an interaction map will be described in more detail later.

Referring back to FIG. 1, the patient criteria fit score determining unit 44 determines a patient criteria fit score for the respective patient interface device. The patient criteria fit score for the respective patient interface device is determined based on patient information other than the geometric fit between the respective patient interface device and the patient's face and/or the additional information associated with the respective patient interface device. For example, the patient criteria fit score can be based on only the patient information, the additional information associated with the respective patient interface device, or a combination of both. Examples of patient information that can be considered are, without limitation, the patient's age, the patient's gender, the patient's condition to be treated, and other patient information (e.g., without limitation, whether the patient is claustrophobic, whether the patient breathes through his or her mouth during sleep, etc.).

Figure 4:
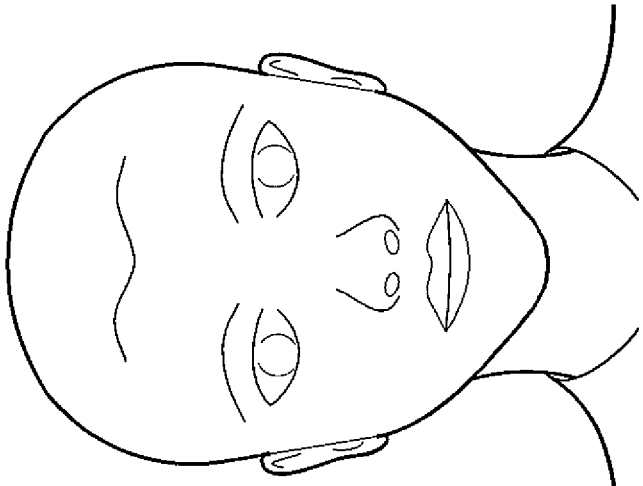
FIG. 4 is a view of a user interface including a patient questionnaire in accordance with an embodiment of the disclosed concept.

The patient information can be generated, for example, by answering questions in a patient questionnaire via the input unit 30. An example of a user interface 200-1 including an exemplary layout of a patient questionnaire is shown in FIG. 4. The user interface 200-1 is generated by the user interface generator 48. The user interface generator 48 will be described in more detail hereinafter.

Figure 3:
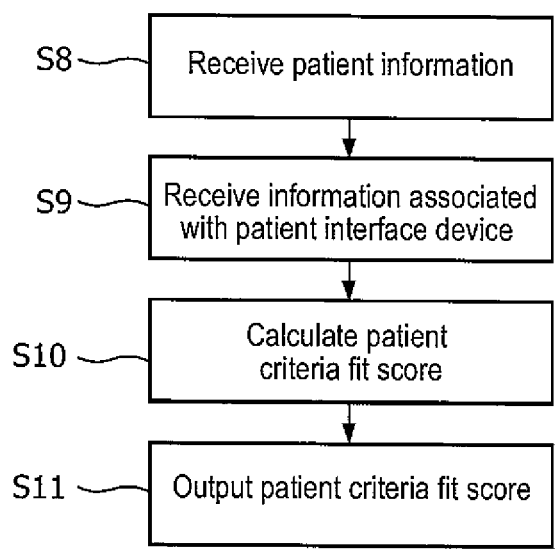
FIG. 3 is a flowchart of a method of determining a patient criteria fit score in accordance with an embodiment of the disclosed concept.

Referring to FIG. 3, an exemplary process of determining a patient criteria fit score for the respective patient interface device is illustrated. The process illustrated in FIG. 3 may be implemented by the patient criteria fit score determining unit 44.

In operation S8, the patient criteria fit score determining unit 44 receives the patient information, and in operation S9, the patient criteria fit score determining unit 44 receives the additional information associated with the respective patient interface device.

In operation S10, the patient fit score determining unit 44 calculates the patient criteria fit score based on the patient information and/or the additional information associated with the respective patient interface device. In more detail, the suitability of the respective patient interface device will be rated for each piece of patient information to arrive at the patient criteria fit score for the respective patient interface device. For example, if the patient information indicates that the patient's condition requires a full face mask for treatment and the additional information associated with the respective patient interface device indicates that the respective patient interface device is a nasal mask, the patient criteria fit score of the respective patient interface device will be adversely affected. It is also contemplated that the patient fit score determining unit 44 can also place different weights on each of the pieces of patient information when determining the patient criteria fit score without departing from the scope of the disclosed concept. It is contemplated that the weightings of each piece of patient information can be pre-set or can be customized by users of the system.

In operation S11, the patient criteria fit score determining unit 44 outputs the patient criteria fit score to the overall fit score determining unit 46.

Figure 5:
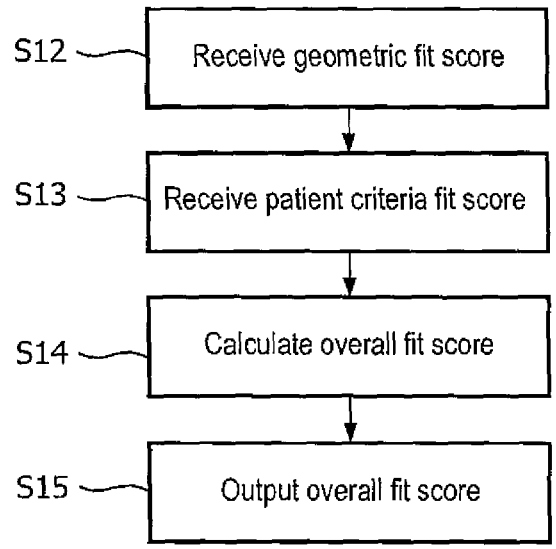
FIG. 5 is a flowchart of a method of determining an overall fit score in accordance with an embodiment of the disclosed concept.

Referring back to FIG. 1, the overall fit score determining unit 46 determines the overall fit score for the respective patient interface device. Referring now to FIG. 5, a process for determining the overall fit score is illustrated. The process illustrated in FIG. 5 may be implemented by the overall fit score determining unit 46.

In operation S12, the overall fit score determining unit 46 receives the geometric fit score for the respective patient interface device from the geometric fit score determining unit 42, and in operation S13, the overall fit score determining unit 46 receives the patient criteria fit score for the respective patient interface device from the patient criteria fit score determining unit 44.

In operation S14, the overall fit score determining unit 46 calculates the overall fit score for the respective patient interface device based on the geometric fit score and the patient criteria fit score. It is contemplated that the overall fit score determining unit 46 can place different weights on each of the geometric fit score and the patient criteria fit score. It is also contemplated that these weights can be pre-set or they can be customized by users of the system.

In operation S14, the overall fit score determining unit 46 outputs the overall fit score for the respective patient interface device to the user interface generator 48.

While operations of the geometric fit score determining unit 42, the patient criteria fit score determining unit 44, and the overall fit score determining unit 46 have been described for one respective patient interface device, it is appreciated that such operations can be repeated to calculate overall fit scores for one or more of the patient interface devices whose 3-D models are stored in the patient interface device information database 20.

Referring back to FIG. 1, the user interface generator 48 generates a user interface for the patient interface device selection system 1 and outputs the generated user interface to the display unit 50. Operation of the user interface generator 48, as well as the user interface, will be described in more detail hereinafter.

Figure 6:
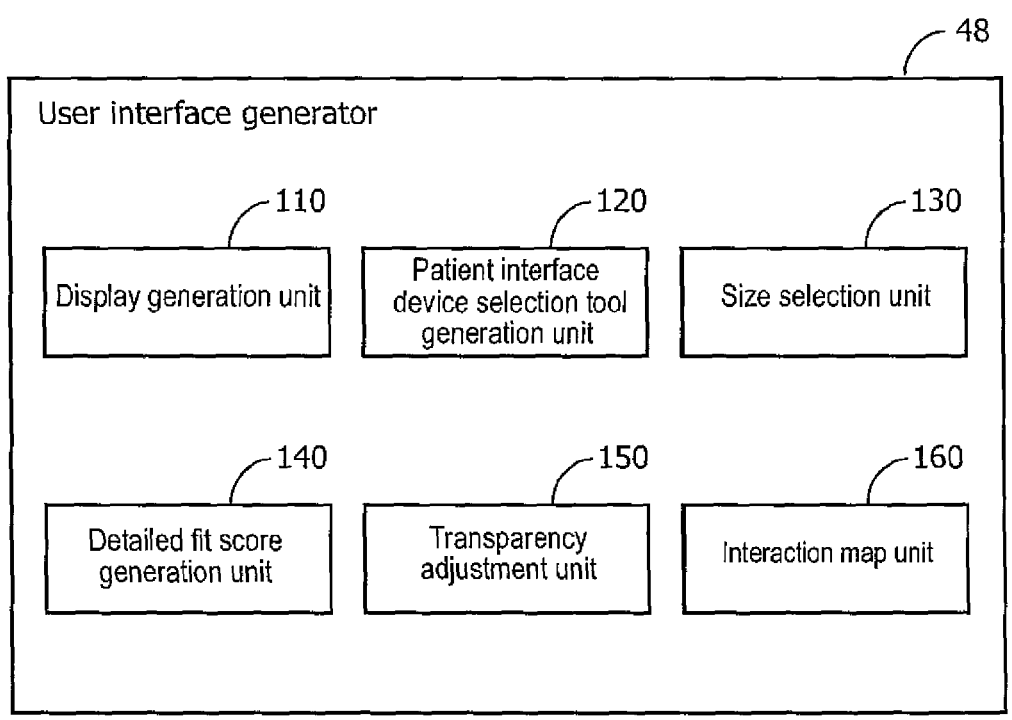
FIG. 6 is diagram of a user interface generator in accordance with an embodiment of the disclosed concept.
Figure 7:
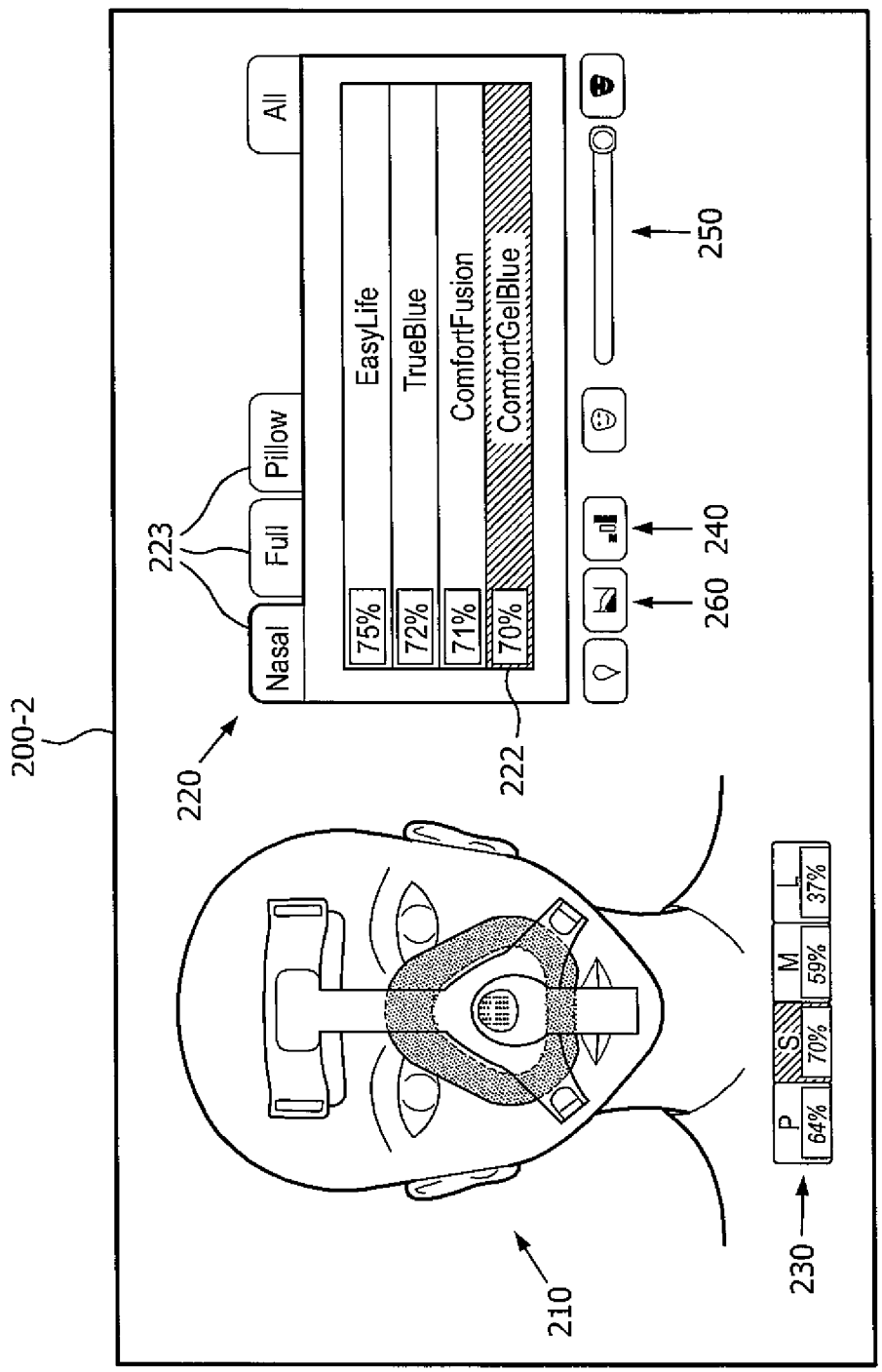
FIG. 7 is a view of a user interface including a 3-D display area and a patient interface device selection area in accordance with an exemplary embodiment of the disclosed concept.

Referring to FIG. 6, the user interface generator 48 is illustrated in more detail, and in FIG. 7, an example user interface 200-2 generated by the user interface generator 48 is illustrated.

The user interface generator 48 includes a display generation unit 110 which generates a display area 210. The display area 210 displays the 3-D model of the patient's face along with a 3-D model of a selected patient interface device fitted to the patient's face. In some exemplary embodiments, the display generation unit 110 can support commands to manipulate images displayed in the display area 210 (e.g., without limitation, pan, zoom, rotate, etc.). The display area 210 allows visual inspection of how the selected patient interface device fits on the patient's face, which can be used in conjunction with the calculated overall fit score to assist with selecting a patient interface device for the patient.

The user interface generator 48 also includes a patient interface device selection tool generation unit 120. The patient interface device selection tool generation unit 120 generates a patient interface device selection display area 220 on the user interface 200-2. The patient interface device selection display area 220 is configured to allow a user to sort patient interface devices and select which patient interface device to display in the display area 210. The patient interface device selection display area 220 is also configured to display the overall fit scores corresponding to the patient interface devices.

In the example shown in FIG. 7, the patient interface device selection display area 220 includes patient interface device identification information 221 (e.g., without limitation, the patient interface device manufacturer and the patient interface device name) for a number of patient interface devices as well as the overall fit scores 222 for the patient interface devices. The patient interface device selection display area 220 also includes a number of filtering tools 223 (e.g., without limitation, tabs) which are configured to allow filtering display of the patient interface devices by their types (e.g., without limitation, nasal, full, or pillow). It is appreciated that any suitable manner of displaying the patient interface device identification information 221 and corresponding overall fit score 222 may be employed without departing from the scope of the disclosed concept. It is also contemplated that any suitable manner of sorting and/or filtering the patient interface devices may be employed without departing from the disclosed concept. For example and without limitation, the patient interface devices may be filtered based upon their availability so that a technician can, for example, hide patient interface devices that are not in stock.

The patient interface device selection display area 220 is also configured to allow selection of one of the patient interface devices to be displayed in the display area 210. Additionally, the patient interface device selection display area 220 is configured to indicate which patient interface device is selected (e.g., without limitation, by highlighting the patient interface device identification information 221 and corresponding overall fit score 222 of the selected patient interface device). The selected patient interface device is then displayed, while fitted on the patient's face, in the display area 210. The user interface generator 48 can be configured to automatically select and display the patient interface device having the highest overall fit score. The user interface generator 48 can also be configured to, upon application of a filter operation, automatically select and display the patient interface device having the highest overall fit score among the patient interface devices remaining after the filtering operation. Furthermore, the user interface generator 48 can be configured to automatically select the patient interface device from among a subset or family of patient interface devices without performing a filtering operation. For example and without limitation, the user interface generator 48 may be configured to select the patient interface device from among the subset or family of patient interface devices upon selection of the subset or family.

The user interface generator 48 also includes a size selection unit 130. The size selection unit 130 generates a size selection tool 230 to be displayed on the user interface

200-2. Many patient interface devices come in different sizes (e.g., without limitation, small, medium, and large) which will affect how they fit a patient's face. For purposes of this disclosure, different patient interface devices having different sizes will be considered distinct patient interface devices. The size selection tool 230 is configured to allow a user of the patient interface device selection system 1 to select a size. Once a size is selected, the patient interface device of the selected size is displayed in the display area 210. It is contemplated that the user interface generator 48 automatically selects the size having the highest overall fit score by default. The user of the patient interface device selection system 1 can then manually select a different size. The size selection tool 230 is also configured to indicate the selected size (e.g., without limitation, by highlighting the selected size). The size selection tool 230 is also configured to display overall fit scores corresponding to each size.

The user interface generator 48 further includes a detailed fit score generation unit 140 which is configured to generate a detailed fit score tool 240 on the user interface 200-2. The detailed fit score tool 240 is configured to allow a user to toggle display of detailed fit score information in a detailed fit score area 241 (See FIG. 8). Detailed fit score information is, without limitation, information on the suitability of each of the criteria used to determine the overall fit score. For example, if the patient's age is used in the determination of the overall fit score, the detailed fit score information would include information on the suitability of the selected patient interface device for the patient's age.

Figure 8:
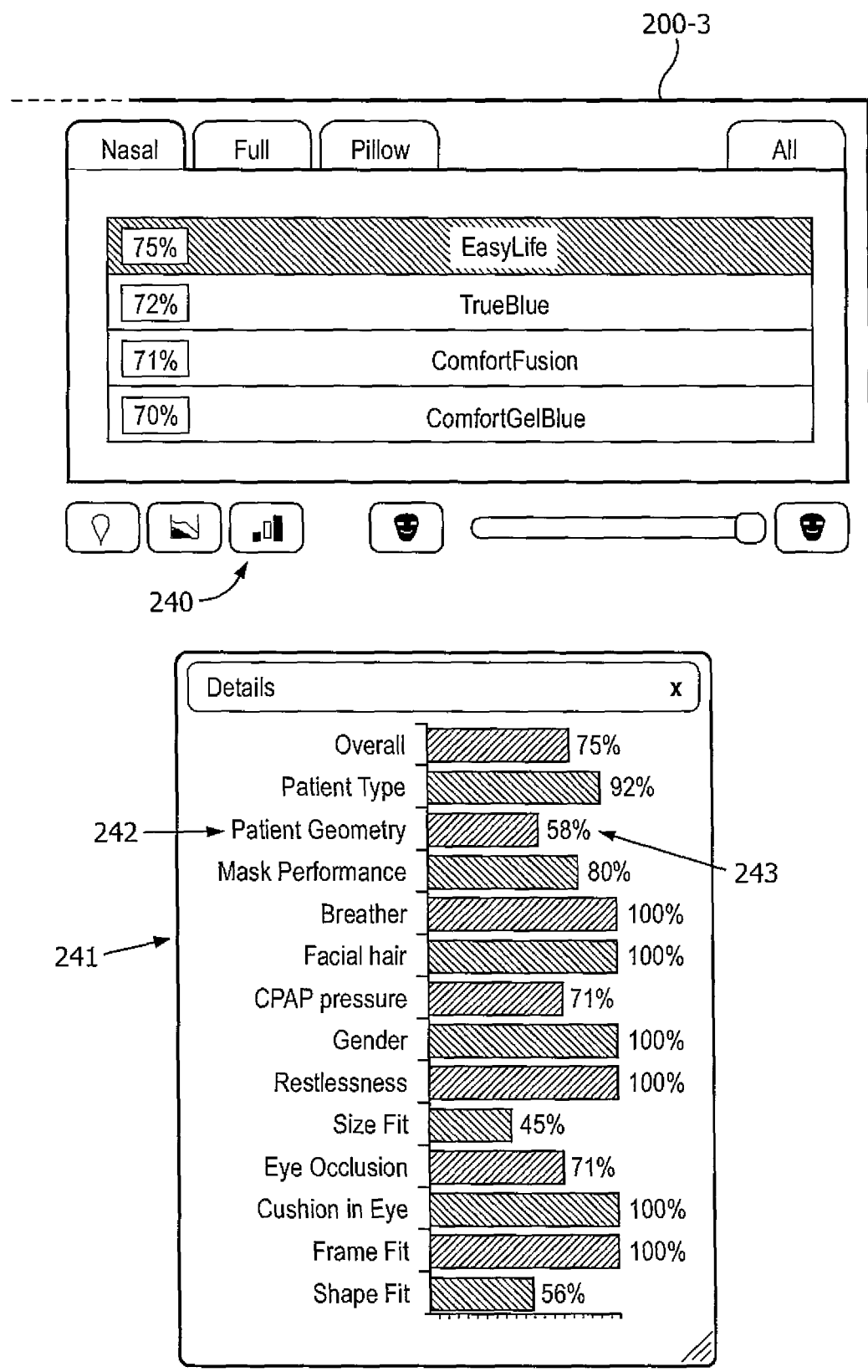
FIG. 8 is a view of a portion of a user interface including a patient interface device selection area and a detailed fit score information area.

To display the detailed fit score area 241, the user of the patient interface device selection system 1 toggles the detailed fit score tool 240. FIG. 8 illustrates the user interface 200-3 when the detailed fit score area 241 is displayed. The detailed fit score area 241 includes criteria identification information 242 for a number of criteria used to determine the overall fit score. The detailed fit score area 241 also includes criteria suitability information 243 which indicates the suitability of each of the displayed criteria. The detailed fit score tool 240 can be employed by the user of the patient interface device selection system to determine reasons why a certain patient interface device received a certain overall fit score. For example, if a patient interface device received a low overall fit score due to it not being suitable to treat a patient's condition, this information can be obtained by looking at the detailed fit score area 241.

Referring back to FIG. 6, the user interface generator 48 also includes a transparency adjustment unit 150. The transparency adjustment unit 150 is configured to generate a transparency adjustment tool 250 on the user interface 200-2 (FIG. 7). The transparency adjustment tool 250 is configured to allow the user of the patient interface device selection system 1 to adjust the transparency of certain components of the patient interface device. Operations of the transparency adjustment unit 150 and the transparency adjustment tool 250 will be described in more detail hereinafter with respect to FIGS. 9-11.

Figure 9:
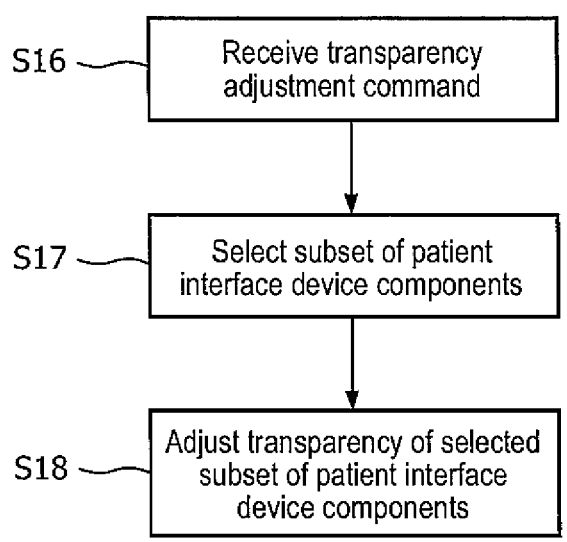
FIG. 9 is a flowchart of a method of adjusting transparency in accordance with an exemplary embodiment of the disclosed concept.
Figure 10:
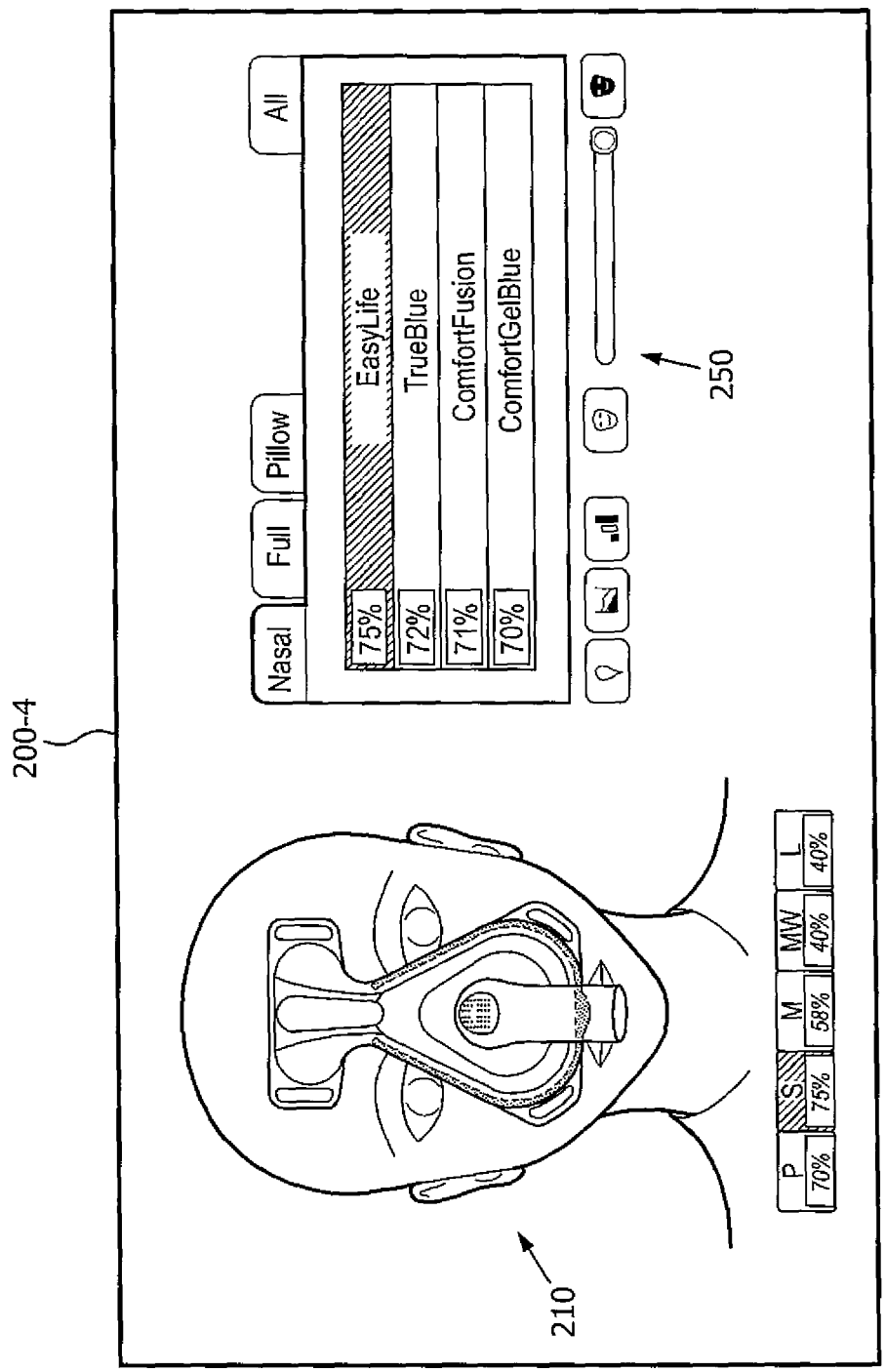
FIGS. 10 and 11 are views of a user interface before and after a transparency adjustment is performed.
Figure 11:
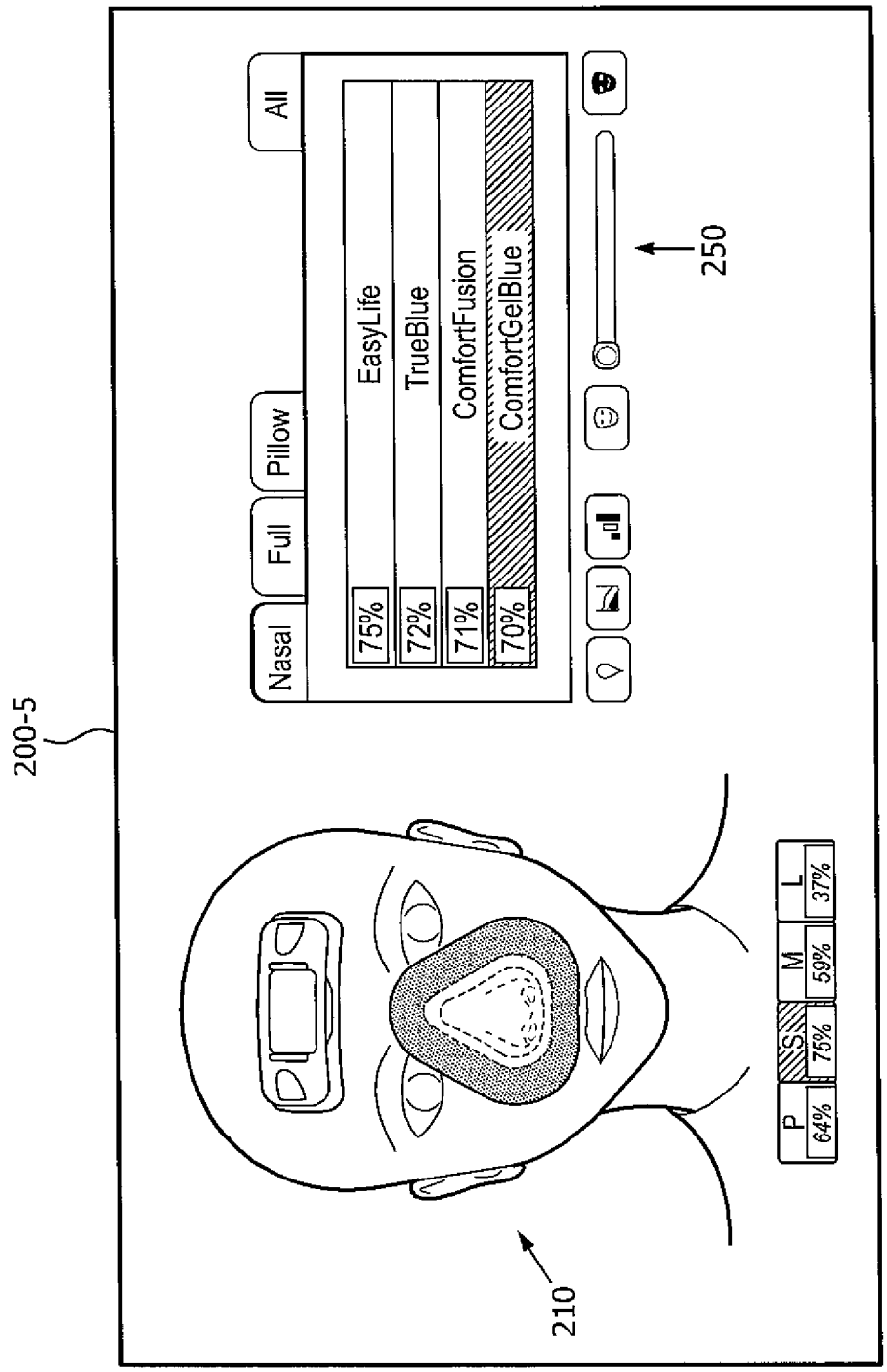

FIG. 9 illustrates a flowchart of a process for adjusting the transparency of selected components of a patient interface device displayed in the display area 210. The process of FIG. 9 can be implemented by the transparency adjustment unit 150. FIG. 10 illustrates the user interface 200-4 prior to adjusting the transparency of the displayed patient interface device and FIG. 11 illustrates the user interface 200-5 after adjusting the transparency of the displayed patient interface device.

Referring to FIG. 9, the transparency adjustment unit 150 receives a transparency adjustment command in operation S16. The transparency adjustment command can be generated, for example, by the user of the patient interface device selection system 1 manipulating the transparency adjustment tool 250. In the example embodiment illustrated in FIGS. 10 and 11, the transparency adjustment tool 250 is a slider bar. However, it is contemplated that any user interface tool suitable for adjusting a value (e.g., without limitation, a dial, a textbox, etc.) can be used without departing from the scope of the invention.

In operation S17, the transparency adjustment unit 150 selects a subset of components of the patient interface device. The selected subset of components will be the components that the transparency adjustment unit 150 performs a transparency adjustment on. In the example embodiment illustrated in FIGS. 9-11, the subset of components of the patient interface device is automatically selected by the transparency adjustment unit 150. However, it will be appreciated that the subset of components of the patient interface device that will have their transparency adjusted can also be manually selected by a user without departing from the scope of the disclosed concept.

In operation S18, the transparency adjustment unit 150 adjusts the transparency of the selected subset of components based on the received transparency adjustment command. The patient interface device with the transparency of the selected subset of the components adjusted is displayed in the display area 110.

Referring to FIGS. 10 and 11, examples of the user interface 200-4,200-5 during a transparency adjustment are illustrated. In FIG. 10, the transparency adjustment tool 250 is slid to the right, thus making components of the patient interface device displayed in the 3-D display area 210 opaque. In FIG. 11, the transparency adjustment tool 250 is slid the to the left, thus making a selected subset of components of the patient interface transparent in the display area 210.

In the example shown in FIGS. 10 and 11, the selected subset of components of the patient interface device is the subset of components that do not touch the patient's skin, and is automatically selected by the transparency adjustment unit 150. When the selected subset of components are made transparent in this example, only the cushion and the forehead cushion are displayed in the display area 210, as shown in FIG. 11. The components of the patient interface device which do not touch the skin of the patient's face generally do not affect the fit of the patient interface device and can obscure the view of the components that do touch the skin of the patient. Thus, making the components of the patient interface device which do not touch the skin of the patient transparent can allow the user of the patient interface device selection system 1 to more easily perform a visual inspection of the fit of the patient interface device.

Referring back to FIG. 6, the user interface generator also includes an interaction map unit 160. The interaction map unit 160 is configured to generate an interaction map tool 260 on the user interface 200-2. (See FIG. 7). The interaction map unit 160 is also configured to generate an interaction map for display in the 3-D display area 210 of the user interface 200-2.

Figure 12:
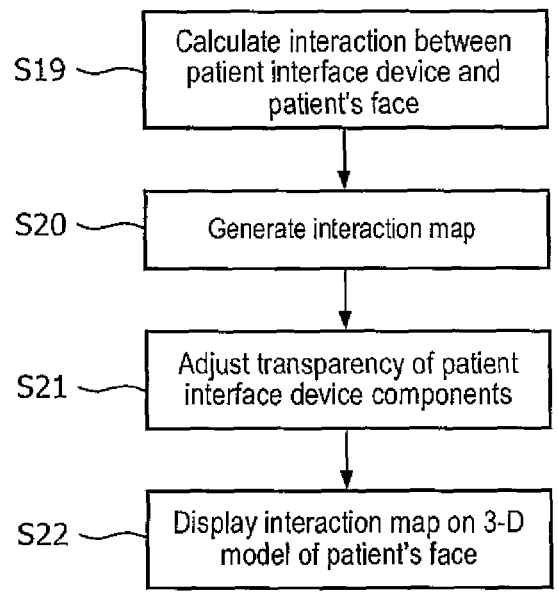
FIG. 12 is a flowchart of a method of creating an interaction map in accordance with an exemplary embodiment of the disclosed concept.

Referring to FIG. 12, a process for generating and displaying an interaction map between a respective patient interface device and the patient's face is shown. The process of FIG. 12 can be implemented by the interaction map unit 160.

The interaction map between the respective patient interface device and the patient's face indicates the amounts of contact pressure the respective patient interface device exerts on the patient's face at different points on the patient's face when the respective patient interface device is fitted to the patient's face.

In operation S19, the interaction unit 160 calculates interaction between the respective patient interface device and the patient's face. In some example embodiments, the interaction between the respective patient interface device and the patient's face is determined based on distances between the contour of the 3-D model of the respective patient interface device and the contour of the 3-D model of the patient's face when the 3-D model of the respective patient interface device is fitted on the 3-D model of the patient's face. For example, a point on the contour of the 3-D model of the patient's face where the contour of the 3-D model of the patient interface device is below the contour of the 3-D model of the patient's face would result in a high interaction level at that point, whereas a point on the contour of the 3-D model of the patient's face where the contour of the 3-D model of the patient interface device is above the patient's face would result in a low interaction level at that point.

Once the interaction map unit 160 calculates the interaction between the respective patient interface device and the patient's face, the interaction map unit 160 generates the interaction map in operation S20. In some exemplary embodiments, the interaction map is a 3-D object which conforms to the 3-D model of the patient's face. The interaction map indicates the interaction between the 3-D model of the patient interface device and the 3-D model of the patient's face, for example, by color coding, such as using darker coloring to indicate areas of high interaction levels and lighter coloring to indicate areas of low interaction levels. In some other exemplary embodiments, the interaction map indicates the interaction between the 3-D model of the patient interface device and the 3-D model of the patient's face by adjusting transparency values of points on the interaction map, such as using lower transparency to indicate areas of high interaction levels and higher transparency to indicate areas of low interaction levels. It yet other exemplary embodiment, the both color coding and adjustment of transparency values of points on the interaction map are used to indicate different levels of interaction. However, it is also appreciated that the interaction map can use any scheme to indicate the amount of interaction at different points on the patient's face (e.g., without limitation, the interaction map can use green coloring to indicate areas of low interaction levels, yellow coloring to indicate areas of medium interaction levels, and red coloring to indicate areas of high interaction levels).

Once the interaction map is generated, the interaction map unit 160 adjusts the transparency of patient interface device components displayed in the display area 210 in operation S21. The interaction map unit 160 can adjust the transparency values of patient interface device interface device components to predetermined values in response to displaying the interaction map and reverse the transparency adjustment (i.e., return the transparency values of the components of the patient interface device to their state prior to the transparency adjustment) in response to hiding the interaction map. In some exemplary embodiments, the interaction map unit 160 adjusts transparency of the patient interface device components so that they are all transparent. In some other exemplary embodiments, the interaction map unit 160 adjusts the transparency of patient interface device components so that they are all semi-transparent. In some further exemplary embodiments, the interaction map unit 160 adjusts the transparency of patient interface device components so that some components are transparent and some other components are semi-transparent. For example, components of the patient interface device that touch the patient's face can be adjusted to be semi-transparent and the components of the patient interface device that do not touch the patient's face can be rendered to be transparent. Adjusting the transparency of the patient interface device makes it easier to see the interaction map when it is displayed in the display area 210.

Figure 13:
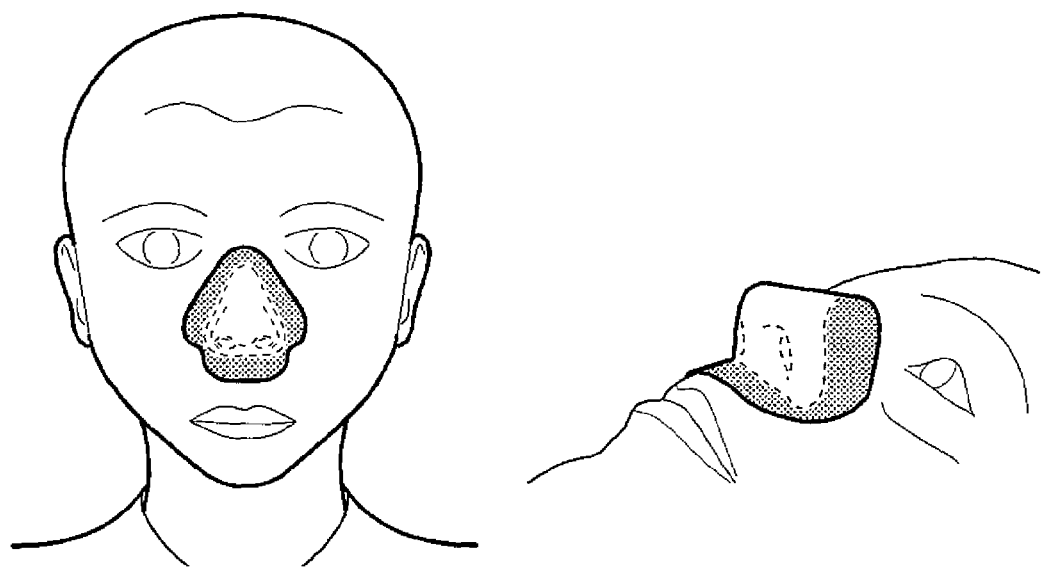
FIG. 13 is two views of displayed interaction maps in accordance with embodiments of the disclosed concept.

In operation S22, the interaction map unit 160 displays the interaction map in the display area 210. In more detail, the interaction map can be a 3-D object that conforms to the shape of the patient's face and is aligned with and placed just above the surface of the patient's face displayed in the display area 210. Two examples of an interaction map displayed with a patient's face are shown in FIG. 13. The displayed interaction map can be used to perform a visual inspection of how well the respective patient interface device fits the patient's face, and in particular, to identify areas of the respective patient interface device which apply higher pressures to the patient's face. This information can also be used, for example, to perform adjustments on the respective patient interface device (if it has components that can be adjusted) to relieve pressure to the patient's face caused by certain areas of the respective patient interface device and improve comfort for the patient.

Figure 14:
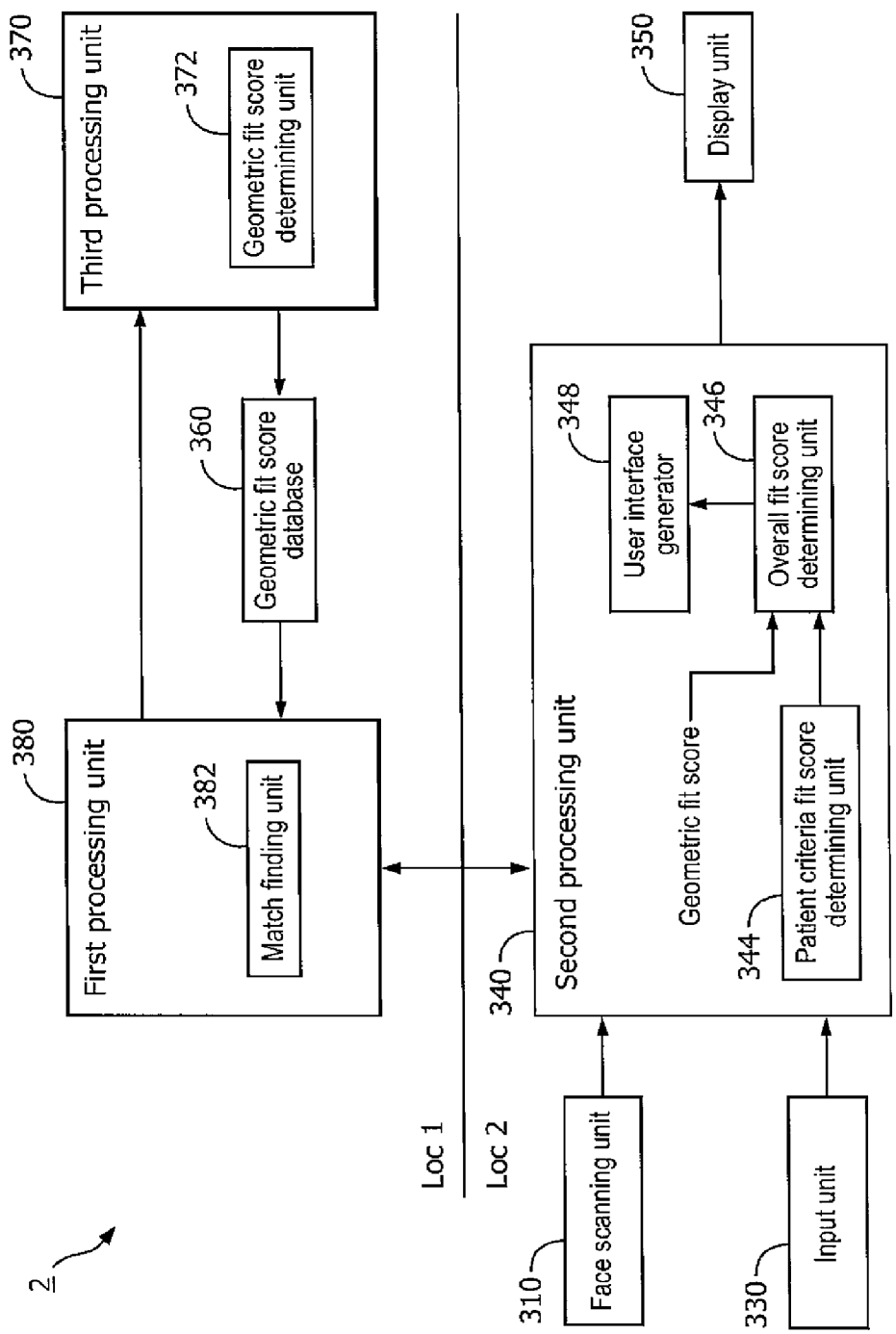
FIG. 14 is a diagram of a system for selecting a patient interface device in accordance with another embodiment of the disclosed concept

Referring to FIG. 14, a patient interface device selection system 2 in accordance with another exemplary embodiment of the disclosed concept is shown. To increase the accuracy of geometric fit scores between a patient's face and a patient interface device, it is desirable to take into account deformation of the patient's face and the patient interface device. One way to account for this deformation is to perform an analysis, such as a finite element analysis, on the patient's face and patient interface device. However, the calculations for this analysis can become extensive, especially when the geometric fit score for each of multiple patient interface devices is being calculated. These calculations can cause a delay in providing results, which can be detrimental if the user desires near-instantaneous results.

Patient interface device selection system 2 addresses this issue. Patient interface device selection system is divided between a first location LOC1 and a second location LOC2. The first location LOC1 includes a first processing unit 380, a geometric fit score database 360, and a third processing unit 370. The second location LOC2 includes a face scanning unit 310, an input unit 330, a second processing unit 340, and a display unit 350.

The geometric fit score database 360 is configured to store a plurality of 3-D models of faces, a plurality of 3-D models of patient interface devices along with additional information associated with the patient interface devices, and the pre-calculated geometric fit score for each of one or more of the patient interface devices for each of one or more of the faces. The 3-D models of the faces are 3-D models of faces of people other than the current patient. The 3-D models of the faces can be obtained in any suitable manner.

The third processing unit 370 is configured to pre-calculate the geometric fit score for one or more of the patient interface devices for one or more of the faces and to provide the results to the geometric fit score database 360 to be stored there. To this extent, the third processing unit 370 includes a geometric fit score determining unit 372 which is configured to pre-calculate the geometric fit score (e.g., without limitation, by performing finite element analysis) for each of the one or more patient interface devices for each of the one or more faces. In this context, the term pre-calculate means that the geometric fit score for each for each of the one or more patient interfaces device for each of the one or more faces have been calculated prior to prior to determining the geometric fit score for each of the one or more patient interface devices for the current patient's face.

Face scanning unit 310 is configured to create and output a 3-D model of a patient's face. Devices are known that are capable of creating and outputting a 3-D model of a patient's face. Examples of such devices include, without limitation, optical scanners, cameras, and push-pin arrays. Face scanning unit 310 is communicatively coupled to remote processing unit 340 and is configured to output the 3-D model of the patient's face to the remote processing unit 340. It is contemplated that face scanning unit 310 and remote processing unit 340 can be at the same location or at different locations without departing from the scope of the disclosed concept. It is also contemplated that the face scanning unit 310 and remote processing unit 340 are communicatively coupled by any suitable means (e.g., without limitation, network, internet, USB, etc.). It is also contemplated that face scanning unit 310 can save the 3-D model of the patient's face to a removable memory device (e.g., without limitation, a USB drive) which can then be read by processing unit 340.

Input unit 330 is configured to receive input of a user of patient interface device selection system 2. Input unit 330 can be any conventional device capable of performing this function, such as, without limitation, a keyboard, keypad, mouse, or touch screen. Input unit 330 is communicatively coupled with remote processing unit 340 by any suitable means (e.g., without limitation, network, internet, USB, etc.).

Second processing unit 340 is configured to receive outputs from face scanning unit 310 and input unit 330. Second processing unit 340 is communicatively connected with first processing unit 380 and outputs the 3-D model of the patient's face to the first processing unit 380.

First processing unit 380 receives the 3-D model of the patient's face and determines the geometric fit score for each of the one or more patient interface devices for the patient's face. To this extent, first processing unit 380 includes a match finding unit 382 which uses pre-calculated geometric fit scores for patient interface devices for one or more of the faces stored in the geometric fit score database 360.

In some embodiments of the disclosed concept, the match finding unit 382 uses a least mean squares method to match the patient's face with the closest matching face stored in the geometric fit score database 360 (e.g., without limitation, by using the 3-D model of the patient's face and the 3-D models of the faces). The match finding unit 382 then uses the pre-calculated geometric fit score for each of one or more of the patient interface devices corresponding to the matched face as the geometric fit score for each of the one or more patient interface devices for the patient's face. The match finding unit 382 can also adjust the pre-calculated geometric fit scores based on geometric differences between the matched face and the patient's face. The match finding unit 382 can also use interpolation to combine pre-calculated geometric fit scores for patient interface devices for multiple faces to determine the geometric fit score of each of the patient interface devices for the patient's face.

In some other embodiments, a deformation effect model can be created by determining the effect of various face shape modes in deforming patient interface devices using principal component analysis on the stored 3-D models of faces. Coefficients of face shape modes for the patient's face can then be determined from the 3-D model of the patient's face. The face shape mode coefficients can then be applied to the deformation effect model to determine the deformation effects of the patient's face on the patient interface devices. Using this method can reduce the amount of calculation needed to model the deformation of patient interface devices.

In addition to determining the geometric fit scores of the patient interface devices for the patient's face, the first processing unit 380 can also output the 3-D model of the patient's face to the third processing unit 370 and control the third processing unit 370 to calculate the geometric fit scores for one or more of the patient interface devices for the patient's face. The third processing unit 370 can then store the calculated geometric fit scores in the geometric fit score database 360 to be used as pre-calculated geometric fit scores for use with other patients. In this manner, the system 2 can continuously populate the geometric fit score database 360.

Once the first processing unit 380 has determined the geometric fit score for one or more of the patient interface devices for the patient's face, the first processing unit 380 outputs the results to the second processing unit 340.

The second processing unit 340 includes a patient criteria fit score determining unit 344, an overall fit score determining unit 346, and a user interface generator 348, which will be described in more detail hereinafter.

The patient criteria fit score determining unit 344 determines a patient criteria fit score of the respective patient interface device for the patient. The patient criteria fit score determining unit 344 operates similar to the patient criteria fit sore determining unit 44 of FIG. 1. However, the patient criteria fit score determining unit 344 of FIG. 14 may receive the additional information associated with the respective patient interface device from the geometric fit score database 360.

The overall fit score determining unit 346 operates similar to the overall fit score determining unit 46 shown in FIG. 1, except that the overall fit score determining unit 346 receives the geometric fit score for each of one or more of the patient interface devices for the patient's face from the first processing unit 380 rather than the geometric fit score determining unit 42. Otherwise, the overall fit score determining unit 346 operates similar to the overall fit score determining unit 46 shown in FIG. 1, and therefore further description of this component is omitted. The user interface generator 348 also operates similar to the user interface generator 48 shown in FIG. 1, and therefore further description of this component is omitted.

It is contemplated that the first location LOC1 and the second location LOC2 are different locations such as, for example and without limitation, a processing center and a caregiver's office. However, it is also contemplated that the first location LOC1 and the second location LOC2 may be combined at a single location without departing from the scope of the disclosed concept. It is also contemplated that the patient interface device selection system 2 is scalable. For example, it is contemplated that one central first processing unit 380, geometric fit score database 360, and third processing unit 370 can correspond to numerous second processing units 340.

Using the first processing unit 380 to determine geometric fit scores based on one or more pre-calculated geometric fit scores, rather than performing the analysis to originally calculate geometric fit scores for the patient's face, allows the user of the patient interface device selection system 2 to receive accurate results quickly.

First, second, and third processing units 380,340,370 340 can each be, for example, any type of processing apparatus such as a microprocessor and a memory unit suitable to store and execute software modules. Geometric fit score determining unit 372, match finding unit 382, patient criteria fit score determining unit 344, overall fit score determining unit 346, and user interface generator 348 can each be embodied as software modules executable by the processing unit on which they reside.

The present disclosed concept can be embodied in an electronic apparatus, such as, for example and without limitation, a mobile device, a mobile computer, a tablet computer, a peripheral device etc. The present disclosed concept can also be embodied as computer readable codes on a tangible computer readable recording medium. The computer readable recording medium is any data storage device that can store data which can be thereafter read by a computer system. Examples of the computer readable recording medium include read-only memory (ROM), random-access memory (RAM), CD-ROMs, magnetic tapes, floppy disks, and optical data storage devices.

It is contemplated that any of the embodiments, combination of embodiments, or modification of embodiments of the disclosed concept described herein can be used by, for example and without limitation, a caregiver or technician, in the process of selecting a patient interface device for a patient.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. An electronic apparatus comprising:
a geometric fit score determining unit configured to receive a 3-D model of a patient's face and a plurality of 3-D models of patient interface devices, to determine one or more landmarks on the 3-D model of the patient's face, and to calculate a geometric fit score for each of one or more of the patient interface devices by using the 3-D model of the patient's face and the 3-D models of the one or more patient interface devices, wherein the geometric fit score determining unit is configured to fit a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device, wherein the fine adjustment includes rotating and translating the 3-D model of the patient interface device to match the contour of the cushion with the contour of the 3-D model of the patient's face;
a user interface generator configured to generate a user interface including a display area configured to display the 3-D model of the patient's face and a 3-D model a patient interface device selected from the plurality of 3-D models of patient interface devices, and a patient interface device selection area configured to display patient interface device identification information and an overall fit score which is calculated for each of the one or more patient interface devices based on the geometric fit score for each of the one or more patient interface devices and to allow a user to select the patient interface device to be displayed in the display area.

2. The electronic apparatus of claim 1, further comprising:
a patient criteria fit score determining unit configured to receive patient information and/or additional information associated with the one or more patient interface devices, and to calculate a patient criteria fit score for each of the one or more patient interface devices based on the patient information and/or the additional information associated with the one or more patient interface devices;
an overall fit score determining unit configured to calculate an overall fit score for each of the one or more patient interface devices based on the calculated geometric fit score and the calculated patient criteria fit score for each of the one or more patient interface devices.

3. The electronic apparatus of claim 1, wherein the geometric fit score determining unit considers deformation of the patient's face and the patient interface devices when calculating the geometric fit score for each of the one or more patient interface devices.

4. The electronic apparatus of claim 1, wherein the user interface generator is configured to generate a patient questionnaire on the user interface for the user to enter the patient information, and the user interface generator is configured to generate the display area and the patient interface device selection area in the user interface in response to the user submitting the patient questionnaire.

5. The electronic apparatus of claim 4, wherein, in response to the user submitting the patient questionnaire, the user interface generator is configured to automatically select a patient interface device having the highest overall fit score from the one or more patient interface devices.

6. The electronic apparatus of claim 1, wherein the user interface generator is configured to generate a size selection tool in the user interface, the size selection tool being configured to allow the user to select a size of the selected patient interface device.

7. The electronic apparatus of claim 6, wherein the size selection tool is configured to display the overall fit score corresponding to each size of the selected patient interface device.

8. The electronic apparatus of claim 1, wherein the user interface generator is configured to generate a detailed fit score display tool in the user interface, the detailed fit score display tool being operable to toggle display of a detailed fit score display area on the user interface, and wherein the detailed fit score display area is configured to display detailed fit score information.

9. The electronic apparatus of claim 1, wherein the patient interface device selection area includes one or more filtering tools operable to filter the one or more patient interface devices that are displayed in the patient interface device selection area of the user interface.

10. The electronic apparatus of claim 1, wherein the user interface generator is configured to generate an interaction map tool and to calculate an interaction map between the 3-D model of the patient's face and the 3-D model of the selected patient interface device, wherein the interaction map tool is operable to toggle display of the interaction map.

11. A method of selecting a patient interface device, the method comprising:
receiving a 3-D model of a patient's face;
receiving a plurality of 3-D models of patient interface devices;
determining one or more landmarks on the 3-D model of the patient's face;
calculating a geometric fit score for each of one or more of the patient interface devices by using the 3-D model of the patient's face and the 3-D models of the one or more patient interface devices, wherein calculating the geometric fit score includes fitting a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device, wherein the fine adjustment includes rotating and translating the 3-D model of the patient interface device to match the contour of the cushion with the contour of the 3-D model of the patient's face;
calculating an overall fit score for each of the one or more patient interface devices based on the calculated geometric fit score for each of the one or more patient interface devices;
generating a user interface, wherein generating the user interface comprises:
generating a display area configured to display the 3-D model of the patient's face and a selected 3-D model of one of the patient interface devices; and
generating a patient interface device selection area configured to display patient interface device identification information and the calculated overall fit score for each of the one or more patient interface devices and to allow a user to select the patient interface device to be displayed in the display area.

12. The method of claim 11, further comprising:
receiving patient information and/or additional information associated with the one or more patient interface devices;
calculating a patient criteria fit score each of the one or more patient interface devices based on the patient information and/or the additional information associated with the one or more patient interface devices; and
calculating the overall fit score for each of the one or more patient interface devices based on the calculated geometric fit score and the calculated patient criteria fit score for each of the one or more patient interface devices.

13. A method for selecting a patient interface device of a plurality of patient interface devices, the method comprising:
creating a 3-D model of a patient's face;
creating 3-D models of each of the plurality of patient interface devices;
providing the 3-D model of the patient's face to a patient interface device selection system;
providing one or more of the 3-D models of the patient interface devices to the patient interface device selection system;
employing the patient interface device selection system to obtain an overall fit score for each of the one or more patient interface devices and to display the 3-D model of the patient's face with one or more of the 3-D models of the patient interface devices fitted thereon; and
selecting one of the patient interface devices, wherein the patient interface device selection system comprises:
a geometric fit score determining unit configured to receive the 3-D model of a patient's face and the one or more 3-D models of patient interface devices, to determine one or more landmarks on the 3-D model of the patient's face, and to calculate a geometric fit score for each of one or more of the patient interface devices by using the 3-D model of the patient's face and the one or more 3-D models of the patient interface devices, wherein the geometric fit score determining unit is configured to fit a respective 3-D model of one of the patient interface devices to the 3-D model of the patient's face by aligning the respective 3-D model of the patient interface device with the determined landmarks on the 3-D model of the patient's face and performing a fine adjustment on the respective 3-D model of the patient interface device, wherein the fine adjustment includes rotating and translating the 3-D model of the patient interface device to match the contour of the cushion with the contour of the 3-D model of the patient's face; and
a user interface generator configured to generate a user interface including a display area configured to display the 3-D model of the patient's face and a selected 3-D model of one of the patient interface devices, and a patient interface device selection area configured to display patient interface device identification information and the overall fit score which is calculated for each of the one or more patient interface devices based on the geometric fit score for each of the one or more patient interface devices and to allow a user to select the patient interface device to be displayed in the display area.

14. Method of providing a patient interface device for a patient, including the steps of:
receiving a 3-D model of a patient's face;
receiving a plurality of 3-D models of patient interface devices;
determining one or more landmarks on the 3-D model of the patient's face;
calculating a geometric fit score for each of one or more of the patient interface devices by using the 3-D model of the patient's face and the 3-D models of the one or more patient interface devices, wherein calculating the geometric fit score includes fitting a respective 3-D model of one of the patient interface devices to the 3-D model of the patient's face by aligning respective 3-D model of the patient interface device with the determined landmarks on the 3-D model of the patient's face and performing a fine adjustment on the respective 3-D model of the patient interface device, wherein the fine adjustment includes rotating and translating the 3-D model of the patient interface device to match the contour of the cushion with the contour of the 3-D model of the patient's face;
calculating an overall fit score for each of the one or more patient interface devices based on the calculated geometric fit score for each of the one or more patient interface devices; and
using the geometric fit score and the overall fit score for manufacturing the patient interface device for the patient, determining the shape of the patient interface device for the patient and/or selecting the patient interface device for the patient from a predetermined set of patient interface devices.

\* \* \* \* \*